United States Patent [19]
Anthony et al.

[11] Patent Number: 5,713,852
[45] Date of Patent: Feb. 3, 1998

[54] ORAL DOSAGE AND METHOD FOR TREATING PAINFUL CONDITIONS OF THE ORAL CAVITY

[75] Inventors: Joyce C. Anthony, Woodside; Liang C. Dong, Mountain View; Susan M. Marks, San Jose; Danusia Szumowski, Palo Alto, all of Calif.

[73] Assignee: Alza Corporation, Palo Alto, Calif.

[21] Appl. No.: 475,233

[22] Filed: Jun. 7, 1995

[51] Int. Cl.$^6$ .................................................. A61M 31/00
[52] U.S. Cl. .................................................. 604/49; 604/890.1
[58] Field of Search ............................ 604/54, 890.1, 604/49, 891.1; 424/435

[56] References Cited

U.S. PATENT DOCUMENTS

| | | | |
|---|---|---|---|
| 3,625,214 | 12/1971 | Higuchi et al. | 128/260 |
| 3,845,770 | 11/1974 | Theeuwes et al. | 128/260 |
| 3,916,899 | 11/1975 | Theeuwes et al. | 128/260 |
| 4,111,201 | 9/1978 | Theeuwes | 128/260 |
| 4,111,202 | 9/1978 | Theeuwes | 128/260 |
| 4,111,203 | 9/1978 | Theeuwes | 128/260 |
| 4,160,020 | 7/1979 | Ayer et al. | 424/15 |
| 4,186,184 | 1/1980 | Zaffaroni | 424/14 |
| 4,200,098 | 4/1980 | Ayer et al. | 128/260 |
| 4,203,439 | 5/1980 | Theeuwes et al. | 128/260 |
| 4,309,996 | 1/1982 | Theeuwes | 128/260 |
| 4,327,725 | 5/1982 | Cortese et al. | 128/260 |
| 4,449,983 | 5/1984 | Cortese et al. | 604/892 |
| 4,612,008 | 9/1986 | Wong et al. | 604/892 |
| 4,713,243 | 12/1987 | Schiraldi et al. | 424/151 |
| 4,740,365 | 4/1988 | Yukimatsu et al. | 424/425 |
| 4,800,056 | 1/1989 | Eckenhoff et al. | 264/129 |
| 4,837,111 | 6/1989 | Deters et al. | 424/473 |
| 4,876,092 | 10/1989 | Mizobuchi et al. | 424/435 |
| 4,900,552 | 2/1990 | Sanvordeder et al. | 424/422 |
| 4,917,894 | 4/1990 | Matthias et al. | 424/440 |
| 4,940,465 | 7/1990 | Theeuwes et al. | 604/892.1 |
| 4,971,790 | 11/1990 | Magruder et al. | 424/78 |
| 5,019,396 | 5/1991 | Ayer et al. | 424/473 |
| 5,021,053 | 6/1991 | Barclay et al. | 604/892.1 |
| 5,057,321 | 10/1991 | Edgren et al. | 424/413 |
| 5,200,195 | 4/1993 | Dong et al. | 424/473 |
| 5,248,310 | 9/1993 | Barclay et al. | 604/891.1 |
| 5,298,256 | 3/1994 | Flockhart et al. | 424/435 |
| 5,433,952 | 7/1995 | Sipos | 424/489 |
| 5,512,293 | 4/1996 | Landrau et al. | 424/449 |
| 5,520,924 | 5/1996 | Chapman et al. | 424/435 |
| 5,573,776 | 11/1996 | Harrison et al. | 424/435 |
| 5,578,315 | 11/1996 | Chien et al. | 424/435 |

FOREIGN PATENT DOCUMENTS

| | | | |
|---|---|---|---|
| 1171691 | 11/1969 | United Kingdom | 424/435 |
| 2 285 299 A | 4/1982 | United Kingdom | 424/435 |
| WO91/01130 | 2/1991 | WIPO . | |
| WO95/15137 | 6/1995 | WIPO . | |

*Primary Examiner*—Corrine M. McDermott
*Assistant Examiner*—Deborah B. Blyveis
*Attorney, Agent, or Firm*—John A. Dhuey; Steven F. Stone

[57] ABSTRACT

A method is described for delivering a beneficial agent, such as an antiinflammatory agent, to the site of a painful condition in the oral cavity of a human being that utilizes an oral dosage form having an immediately releasable topical anesthetic and a sustained release beneficial agent. The topical anesthetic is released substantially independently of the beneficial agent to provide immediate pain relief and the application of the beneficial agent is continued over a long period of time.

8 Claims, 4 Drawing Sheets

ORAL DOSAGE AND METHOD FOR TREATING PAINFUL CONDITIONS OF THE ORAL CAVITY

1. TECHNICAL FIELD

This invention relates to the treatment of painful conditions of the oral cavity. More particularly, the invention relates to an improved oral dosage form comprising an anesthetic overcoat for immediate release to the site of buccal administration and a sustained release formulation of a beneficial agent effective to treat the painful condition.

2. BACKGROUND ART

Recurrent Apthous Ulcers (RAU), commonly called canker sores, is one of the most common oral mucosal diseases. It is not uncommon for the severe sufferer to have multiple sores on the buccal mucosa and under the tongue. These sores last from 1 to 4 weeks and are extremely painful. Lichen planus is another relatively common chronic inflammatory skin disease with intra-oral sites of infection. In some cases with this latter affliction, the epithelium ulcerates, giving rise to localized pain. Typical methods of treatment for these exemplary painful conditions of the oral cavity include ointments, gels, pastes, and rinses/mouthwashes which include anesthetics and/or corticosteroids.

The action of saliva and swallowing by the patient effectively reduces the concentration of the beneficial agent of drug along the buccal membranes of the oral cavity and further causes much of the beneficial agent to be swallowed, thereby removing the beneficial agent from the site where it is needed. This has been a particular problem in treating painful conditions of the oral cavity which require constant local administration of a beneficial agent. Thus when the anti-canker sore beneficial agents are administered as described above, the agents are cleared from the oral cavity in a matter of minutes. While the duration of beneficial agent delivery is increased somewhat using slowly dissolving pastilles and tablets, typically these dosage forms release beneficial agent for no more than about 15 to 20 minutes. Accordingly, these dosage forms require frequent repetitive dosing (e.g., gargling every five minutes or taking a lozenge 3-4 times per hour) in order to effectively treat the condition. As a result, there is a need for a means for continuously treating painful conditions of the oral cavity over a longer treatment period.

A proposed solution to the problem of short duration of beneficial agent delivery from rinses, pastilles, and tablets, has been an oral dosage form comprised of a hydrophilic polymer having a beneficial agent dispersed therein. When placed between the cheek and gum of a patient, the hydrophilic polymer absorbs moisture from the buccal membrane, eventually adhering itself to the membrane surface. While it is desirable from the standpoint of patient comfort and convenience to adhere the delivery platform directly to the buccal membrane, a problem may arise when delivering a beneficial agent which causes irritation. When delivering an irritating beneficial agent, these dosage forms tend to magnify the irritation is since they adhere to the buccal membrane and maintain a high concentration of the irritating beneficial agent at a single membrane site. This problem is magnified even more when the site of treatment is a painful sore, as in RAU, since contacting the sore with the dosage form increases the pain experienced by the patient. Thus there is a need for a dosage form which reduces the discomfort that accompanies treating painful conditions of the oral cavity.

Another proposed solution to treating painful conditions of the oral cavity is the use of osmotic dosage forms for sustained delivery of beneficial agents to treatment site. See U.S. Pat. Nos. 5,021,053 issued to Barclay et al, 5,248,310 issued to Barclay et al, and 5,200,195 issued to Dong et al all of which are incorporated by reference herein. These dosage forms include a semipermeable membrane, with an exit passageway, which surrounds a beneficial agent formulation and an expandable driving member. The driving member comprises a hydrophilic polymer that imbibes water and expands within the fixed volume of the semipermeable membrane, pushing the beneficial agent out through the exit passageway. U.S. Pat. No. 5,200,194 issued to Edgren et al, discloses an oral osmotic dosage form having a high fluxing although fragile osmotic membrane. A fibrous support material is provided so that the membrane can withstand oral cavity conditions of use. However, when such dosage forms are used in the mouth, the treatment site may be irritated by the high concentrations of beneficial agent as it is being delivered. Furthermore, if the site of treatment is an ulcer or canker sore, the positioning of the dosage form against the sore may be extremely aggravating or painful. Thus there is a need to anesthetize the treatment site before providing a sustained release dosage form.

DISCLOSURE OF THE INVENTION

Accordingly, it is an aspect of the invention to provide a dosage form capable of anesthetizing the treatment site in the oral cavity and delivering sustained release beneficial agent thereto.

It is another aspect of the invention to provide immediate release of a is topical anesthetic to an oral treatment site and concurrently provide sustained release of a beneficial agent to treat the same site.

It is another aspect of this invention to provide a sustained release dosage form for the controlled delivery of a beneficial agent to the oral cavity of an animal, and in particular a human, for a period of time consistent with the effects of a topical anesthetic.

These and other aspects of the invention are provided by an oral dosage form having an anesthetic overcoat and a sustained release beneficial agent core. The core includes a sustained release dosage, a semipermeable wall surrounding a beneficial agent and an expandable driving member. The driving member includes a layer of a hydrophilic polymer, which expands to diminish the volume occupied by the beneficial agent, thereby delivering the beneficial agent from the device at a controlled rate over a period of time while the site is anesthetized.

Other aspects, features, aspects and advantages of the invention will be more apparent to those versed in the art from the following detailed specification taken in conjunction with the figures and the accompanying claims.

MODES FOR CARRYING OUT THE INVENTION

This invention concerns an improved oral dosage form for controlled and sustained release of a beneficial agent to treat painful conditions of the oral cavity of an animal, such as a human. An immediate release anesthetic overcoat provides initial pain relief at the site of treatment associated with the disorder and reduces the discomfort arising during treatment. Preferably, the sustained release core comprises an osmotically driven dosage form and most preferably comprises an expandable driving member and a layer of a non-anesthetic beneficial agent.

The invention also includes a method for treating oral disorders by applying an immediate release topical anesthetic to the site of treatment and applying a sustained release oral dosage form to the anesthetized site to treat the sores at the selected site.

Figure 1:
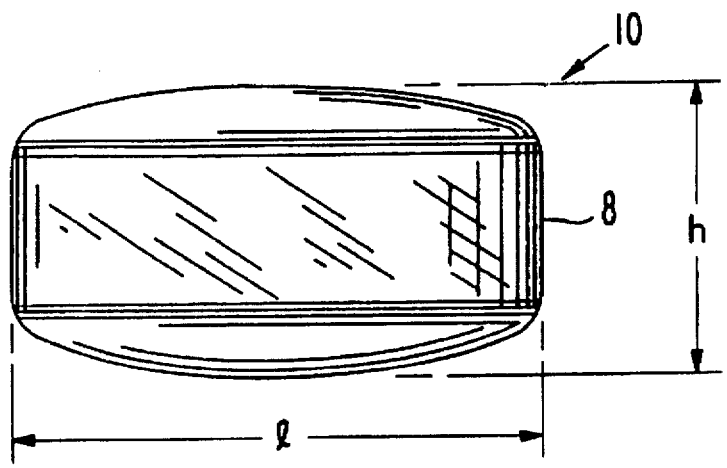
FIG. 1 is a side view of a preferred embodiment of an osmotic dosage form for administering a beneficial agent into the oral cavity of an animal.
Figure 2:
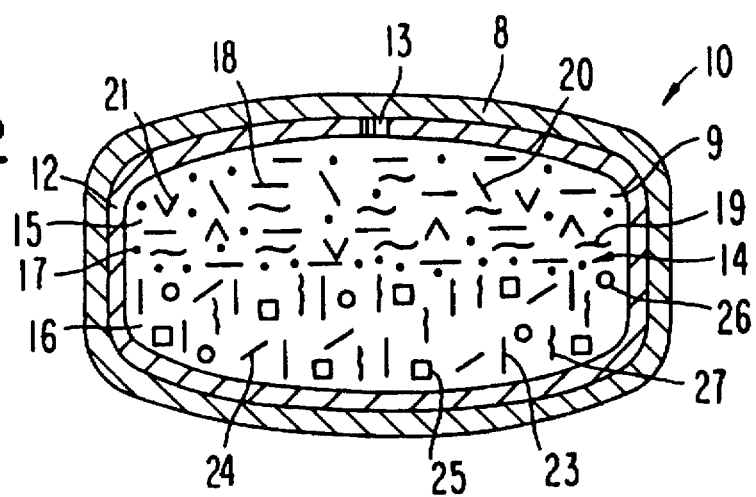
FIG. 2 is a cross-sectional view of the dosage form of FIG. 1.
Figure 3:
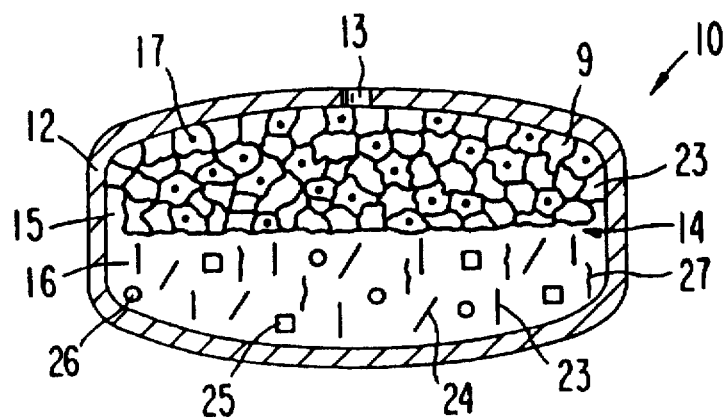
FIG. 3 is a cross-sectional view of the dosage form of FIG. 1 with the oral dosage form in an operating mode and exhibiting a flocculated hydrophilic polymer above its lower critical solution temperature.

Although the sustained release portion of the oral dosage form can be formed from any sustained release composition known to the art, osmotic dosage forms because of their precise control of delivery rate and duration are preferred. Turning now to the drawings, one example of a preferred oral osmotic device is shown in FIGS. 1–3 and is indicated by the numeral 10. as best shown in FIGS. 1 and 2, oral dosage form 10 is comprised of a immediate release topical anesthetic dispersed in overcoat 8 for anesthetizing the site of the painful conditions in the oral cavity. The overcoat 8 surrounds a sustained release core 9 (shown in FIGS. 2 and 3) for providing sustained controlled delivery of a beneficial agent. The start-up of delivery of the sustained release core occurs during the period of anesthesia provided by the anesthetic.

The immediate release anesthetic overcoat 8 comprises a topical, local anesthetic and a binding agent to adhere the anesthetic to the sustained release core. The anesthetic overcoat 8 provides an immediate release dose of an anesthetic which is quickly delivered to the patient upon placement in the oral cavity at the site of the sore. Generally the overcoat 8 is completely dissolved by patient sucking within fifteen to thirty minutes, resulting in an immediate and continuous anesthetizing of the treatment site over a duration of anesthesia. "Immediately" anesthetizing is defined as providing pain relief from 0.1 minute to 10 minutes from insertion in the mouth. Preferably the pain relief is provided within 1–8 minutes and most preferably between 1–5 minutes. The time of initiation and duration of relief will vary with the type of anesthetic used and the concentration of the anesthetic provided in overcoat 8. Preferably, sufficient anesthetic is provided to maintain anesthesia for the duration of beneficial agent release from the sustained release core 9. More preferably sufficient anesthetic is provided to maintain anesthesia for at least 15 minutes to ninety minutes. Most preferably sufficient anesthetic is provided to maintain anesthesia for at least the start-up period of the sustained release device.

The topical anesthetic used in overcoat 8 can be any known local anesthetic agent including lidocaine, procaine, bupivacaine, mepivacaine, etidocaine, dibucaine, chloroprocaine, xylocaine, prilocaine, benzocaine tetracaine, cocaine, dyclonine, and pramoxine, combinations thereof. Of these, hydrophobic local anesthetics which are poorly soluble in water and, consequently, are generally slowly absorbed are most preferred. These hydrophobic anesthetics can be applied directly to the sores. They can also, in one preferred embodiment, remain localized for long periods of time to produce a sustained anesthetic action. One embodiment, chemically, is an ester of para-aminobenzoic acid which is characterized by increased hydrophobicity and thus insolubility of the agent. One most preferred local anesthetic is benzocaine (ethyl aminobenzoate). Another advantage in using esters of para-aminobenzoate acids is a reduced potential for allergic reactions. The actual amount of the anesthetic in the anesthetic overcoat will vary with the specific anesthetic used.

Suitable binders for overcoat 8 are well known in the art and can be selected for their ability to provide a smooth coating and spray characteristics, in the event the overcoat 8 is sprayed on during the manufacturing process. Representative binders include polyvinylpyrrolidone and hydroxypropylmethylcellulose.

In one preferred embodiment, the overcoat comprises 0 to 60 wt % benzocaine, 40 to 90 wt % hydroxypropylmethylcellulose, (HPMC 603) and 10% to 12.5% hydroxypropylcellulose (Klucel EF). In one more preferred embodiment, the overcoat comprises 40 wt % to 50 wt % benzocaine, 37.5 wt % to 45 wt % hydroxypropylmethylcellulose, (HPMC 603) and 10% to 12.5% hydroxypropylcellulose (Klucel EF). The overcoat weighing between 25 to 30 mg/dosage form is preferred. One example of a preferred oral osmotic dosage form is described in U.S. Pat. No. 5,200,195, which is incorporated by reference. The overcoat has a preferred thickness of between 1 to 4 mils.

Oral dosage form 10 continuously delivers therapeutically effective amounts of the beneficial agent 17 to the anesthetized oral treatment site for extended periods of time. In one embodiment, an oral dosage form 10 provides a release of 90% of the beneficial agent in a time interval T (i.e., $T_{90}$) of one to three hours.

In addition to anesthetic overcoat 8, oral dosage form 10 comprises a semipermeable membrane wall 12 surrounding a compartment 14 containing the beneficial agent 17 and expandable driving layer 16. An exit passageway 13 is provided for delivery of a solution or suspension of agent 17 into the environment of use, i.e., the oral cavity. When dosage form 10 is placed in the mouth of a patient, water (e.g. saliva) permeates across the semipermeable membrane and into the internal compartment 14 causing the expandable driving member 16 to swell and expand and thereby push the agent 17 from the dosage form.

Herein the term beneficial agent includes any physiologically or pharmacologically active substance that produces a local or systemic effect when administered to the oral cavity of a human, specifically including a substance effective in the treatment of painful conditions of the oral cavity.

For treating painful conditions in the oral cavity, insoluble or poorly soluble beneficial agents are preferred because the treatment site is on the surface of the mucosa. Furthermore, the more hydrophobic the agent, the longer the anesthetic effect will last. Anti-inflammatory beneficial agents such as topical corticosteroids are preferred. Typical corticosteroids include hydrocortisone, hydrocortico-sterone acetate, cortisone acetate, triamcinolone, and budesonide. Exemplary beneficial agents that are poorly soluble in water and that can be delivered by the devices of this invention include beclomethasone, analogs, homologs, agonists, antagonists and other compounds related to beclomethasone dipropionate. Numerous analogs, homologs, agonists, antagonists and other compounds related to beclomethasone, including those disclosed in GB Patents Nos. 912,378 and 901,093, which are incorporated by reference, and salts and esters thereof. For the purpose of the invention, the phrase an insoluble agent is one that dissolves in the range of 0.01–25 mg agent per ml. A poorly soluble agent is one that dissolves in the range of about 25 mg to 150 mg of agent per ml of fluid. While the presently preferred embodiments have been described with reference to insoluble or poorly soluble agents, it is to be understood the device can be used to deliver other agents.

Typical methods used for the measurement of solubility are chemical and electrical conductivity. Details of various methods for determining solubilities are described in *United States Public Health Service Bulletin*, No. 67 of the Hygienic Laboratory; *Encyclopedia of Science and Technology*, Vol. 12, pages 542 to 556, 1971, published by McGraw-Hill, Inc.; and *Encyclopedia Dictionary of Physics*, Vol. 6, pages 547 to 557, 1962, published in Pergamon Press, Inc.

Oral dosage form 10 of FIGS. 1–3 is designed for oral use, that is, for releasing a locally therapeutic agent in the oral cavity of an animal, such as a human, over an extended period of time. Because the device is designed to be retained in the mouth for periods on the order of about 0.5 to 3 hours, the device must have an exterior shape which is comfortably retained in the mouth. It has been found that an oblong or elliptically shaped oral dosage form 10 is preferred from a comfort standpoint. As shown in FIGS. 1 and 2, oral dosage form 10 has a length 1, a width w (not shown), and a height h. It has been found that oral dosage form 10 having an aspect ratio, which ratio is the ratio of 1:w, of about 1.2:1 to about 3:1 are most comfortably retained in the mouths of humans. Preferably, the oral dosage form 10 has an aspect ratio of about 1.3:1 to about 2:1, and most preferably about 1.5:1 to about 1.7:1. In addition, in order to fit comfortably between the cheek and gum of a patient, the device preferably has a major axis of 1.0 to 1.5 cm, and most preferably between 1.27 to 1.30 cm, and a minor axis of 0.5 cm to 1 cm and most preferably between 0.70 to 0.73 cm.

Osmotic delivery oral dosage form 10 can be manufactured with a wall 12 formed of a material that does not adversely affect the agent 17 (e.g., a beneficial agent) and the osmagent, if any is present. The material forming wall 12 should also not adversely affect the buccal tissues of the patient and should be insoluble in fluids naturally present in the oral cavity. In addition, the material forming wall 12 is permeable to the passage of aqueous fluids, i.e., water and biological fluids naturally present in the oral cavity (e.g., saliva), while remaining essentially impermeable to the passage of agents, including beneficial agents, osmagents, and the like.

Typical materials for forming wall 12 include semipermeable polymers known to the art as osmosis and reverse osmosis membranes, such as cellulose acylate, cellulose, diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethylaminacetate, cellulose acetate ethyl carbamate, cellulose acetate chloracetate, cellulose dipalmatate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, cross-linked selectively semipermeable polymers formed by the co-precipitation of a polyanion and a polycation as disclosed in U.S. Pat. Nos. 3,173,876; 3,276,586; 3,541,005; 3,541,006; and 3,546,142, semipermeable polymers as disclosed by Loeb and Sourirajan in U.S. Pat. No. 3,133,132, lightly cross-linked polystyrene derivatives, cross-linked poly (sodium styrene sulfonate), poly(vinylbenzyltrimethyl ammonium chloride), cellulose acetate having a degree of substitution up to 1 and an acetyl content up to 21%, cellulose diacetate having a degree of substitution of 1 to 2 and an acetyl content of 21 to 35%, cellulose triacetate having a degree of substitution of 2 to 3 and an acetyl content of 35 to 44.8%, as disclosed in U.S. Pat. No. 4,160,020.

In accordance with a preferred embodiment of the present invention, wall 12 is comprised of a relatively high flux membrane material. The high flux membranes are useful when the oral dosage form 10 is designed to deliver a beneficial agent over a relatively short period of time (e.g., up to about 3 hours). Generally, high flux semipermeable membrane materials have a thickness of about 1 to 10 mils; a porosity of about 30 to 70 vol. %; and a fluid permeability greater than about $2\times10^{-4}$ cm mil/atm hr. High flux semipermeable membrane materials indirectly shorten the beneficial agent delivery period by enhancing the imbibition of fluid across the membrane and thus the rate of expansion by the expandable driving member.

High flux semipermeable membranes suffer increased incidence of fracturing when exposed to normal delivery conditions in the oral cavity, e.g., chewing and biting. However, reducing the viscosity of the beneficial agent reduces the pressure exerted upon the membrane since less pressure is required to effect passage through the exist passageway than higher viscosity beneficial agent formulations. Another factor in reducing the incidence of membrane fracturing was discovered to be a reduction in the size of the sustained release core from a major axis length of 1.50 to 1.27 and a minor axis length from 0.79 to 0.70 aided in the reduction of wall fracturing.

Internal compartment 14 contains a bilayer core comprised of a beneficial agent containing layer 15 and a expandable driving member or hydrophilic push layer 16. First layer 15 comprises a beneficial agent 17, represented by dots, which is present in layer 15 in a therapeutically effective amount for producing an intended therapy. Generally, layer 15 comprises 10 nanograms, ng, to 1200 milligrams, mg, of beneficial agent 17 for producing a therapeutic effect.

Beneficial layer 15 comprises 15 wt % to 60 wt % of a hydrophilic polymer 18, represented by dashes, possessing a lower critical solution temperature. Generally, in one example operable for the purpose of the invention, the hydrophilic polymer possesses a lower critical solution temperature of 35° C. to 50° C., however, other temperatures are within the scope of the invention. The phrase "lower critical solution temperature", as used for the purpose of this invention denotes the temperature at which the hydrophilic polymer 18 undergoes an in situ flocculation to provide a floc with beneficial agent 17 dispersed in the floc. The term "flocculation", as used herein means polymer 18 aggregates or precipitates in situ, in solution at the lower critical solution temperature. The term "floc" refers also to the flocculent mass formed as an aggregate or precipitate comprising beneficial agent 17 at the lower critical solution temperature.

The use of floc with a dispersed beneficial agent 17 reduces the viscosity of the beneficial agent formulation 17, reducing the stress applied to the semipermeable wall 12, as compared to delivery systems using polyoxyethylene polymer. Suspending agents are of particular value when the beneficial agent is a hydrophobic beneficial agent, such as beclomethasone dipropionate, to reduce the settling of the beneficial agent within the formulation layer.

Beneficial agent layer 15 comprises a dehydrating agent 19, represented by wavy lines. The dehydrating agent 19 shifts the solubilizing temperature of the hydrophilic polymer so that a polymer that may otherwise be soluble at 37° C. is insoluble at that temperature. The dehydrating agent 19 possesses a greater affinity for water compared with lower critical solution temperature hydrophilic polymer 18. Dehydrating agent 19 may be selected from the group consisting of an electrolyte and a nonelectrolyte, that depresses the lower critical solution temperature of polymer 18 to below body temperature of 32° C. by dehydrating polymer 18 and consequently enhancing polymer-polymer interaction and in situ flocculation. The depressing property of an electrolyte depends on the ability of its ions to hydrate in the presence of water, and the higher its affinity for water the higher depressing efficacy of the electrolyte. For example, cations and anions can be arranged in a lyotropic series of decreasing dehydrating ability as follows: $Mg^{++}>Ca^{++}>Sr^{++}>Ba^{++}>Li^+>Na^+>K+>NH_4^+>Rb^+>Cs^+>Citrate^{3-}>SO_4^{2-}>Cl^->NO_3^->I^->CNS^-$, as reported in *Introduction to Colloid Surface Chemistry*, Third Edition, by D. J. Show, Butterworths, London, (1980). The affinity of a dehydrating agent for water can be ascertained by solubility parameter determinations as reported in *CRC Handbook of Chemistry and Physics*, 69th Edition, (1988–1989), published by CRC Press, Inc.; and in *Chemical Technician's Ready Reference Handbook*, Second Edition, pg 413–415, (1981), published by McGraw-Hill, Inc. The nonelectrolytes for depressing the lower critical solution temperature comprise a polyhydroxy compound and a saccharide. Representative of polyhydroxy compounds comprise mannitol, sorbitol, maltitol, lactisol, maltotriitol, maltoletraitol, maltopentaitol, maltohexaitol, maltoheptaitol, 1,2,6-hexanetriol, pentaerythritol, 1,2,5 pentanetriol, and 1,2,4-butanetriol. The polyhydroxy compounds comprise diols, triols, tetraols, pentaneols, hexaneols, heptaneols, and octaneols. Representative saccharides comprise pentoses and hexoses, such as glucose, fructose, mannose, galactose, aldohexose, aldopentose, allose, altrose, talose, gulose, idose, and glucosone. Generally, first composition 15 comprises 10 wt % to 45 wt % of dehydrating agent 19, and in a presently preferred embodiment from 25 to 40 wt %.

Layer 15 preferably comprises 0.1 wt % to 10 wt % of a surfactant 20. The surfactants act as an emulsifying or suspending agent. The surfactants comprise propylene glycol alginate, propylene glycol agarose, propylene glycol ghatti, propylene glycol tragacanth, propylene glycol pectin, propylene glycol palmitate, propylene glycol oleate, propylene glycol stearate, propylene glycol lactate, propylene glycol maleate, propylene glycol malate, and propylene glycol tartrate; first layer 15 comprises 0.01 wt % to 22 wt % of a binder 21 comprising dextrin, polyvinylpyrrolidone, starch paste or gelatin. Layer 15 more preferably comprises a lubricant for reducing adhesiveness of the composition to the surface of dies and punches. The lubricant may be selected from aluminum stearate, stearic acid, calcium oleate, magnesium stearate, glyceryl behenate, potassium stearyl fumarate, and/or sodium stearyl fumarate.

Layer 16 comprises a hydrophilic polymer 23. The hydrophilic polymer exhibits the ability to swell and expand 2 to 60 fold in the presence of imbibed water and biological fluid, and thereby push the materials in layer 15 from dosage form 10. The hydrophilic polymers retain a significant volume of water or biological fluid within the polymer structure. The hydrophilic polymers can be non cross-linked, or they can be lightly cross-linked. The cross-links can be covalent, physical (microcrystalline), hydrogen bonding or ionic bonds with the polymer possessing the ability to swell in the presence of fluid, and when cross-linked, it will not dissolve in the fluid. The polymer can be of plant, animal or synthetic origin. Polymeric materials useful for the present purpose include poly(hydroxyalkyl methacrylate) having a molecular weight of from 5,000 to 5,000,000; poly (vinylpyrrolidone) having a molecular weight of from 10,000 to 360,000; anionic and cationic hydrogels; poly (electrolyte) complexes; poly(-vinyl alcohol) having a low acetate residual; a water-swellable copolymer produced by a dispersion of finely divided copolymer of maleic anhydride with styrene, ethylene, propylene, or isobutylene; water swellable polymer of N-vinyl lactams; poly(vinyl alcohol) cross-linked with glyoxal, formaldehyde or glutaraldehyde; Cyanamer® polyacrylamide cross-linked with indene maleic anhydride; Carbopol® acidic carboxy polymer and its salt derivatives; polyacrylamides; water-swellable indene maleic anhydride polymers; Goodrite® polyacrylic acid having a molecular weight of 80,000 200,000; Polyox® polyethylene oxide polymers having a molecular weight of 100,000 to 7,000,000, and greater; starch graft copolymers; polyanions and polycations exchange polymers; starch-polyacrylonitrile copolymers. Aqua-Keep® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000; copolymers of N-vinyl lactam with N-vinyl piperidione; Water-Lock® starch-graft poly(iodine acrylate-co-acrylamide); sodium carboxymethylcellulose; and the like.

In one preferred manufacture, hydrophilic polymer 23 comprises a hydrogel having a 15,000 to 7,500,000 molecular weight, more preferably a polysaccharide. The polysaccharide hydrogels useful for making an expandable, push second composition comprise natural gums, seaweed extract, plant exudate, agar, agarose, algin, sodium alginate, potassium alginate, carrageenan, kappa-carrageenan, lambda-carrageenan, fucoidan, furcellaran, laminarin, hypnea, eucheuma, gum arabic, gum ghatti, gum karaya, gum tragacanth, guar gum, locust bean gum, quince psyllium, flax seed, okra gum, arabino-galactin, pectin, xanthan, scleroglucan, dextran, amylose, amylopectin, dextrin, acacia, karaya, guar, a swellable mixture of agar and carboxymethyl cellulose; a swellable composition comprising methyl cellulose mixed with a sparingly cross-linked agar; a blend of sodium alginate and locust bean gum; and the like. The hydrophilic polymers 23 comprising the hydrogels are known to the prior art in U.S. Pat. Nos. 3,865,108; 4,002,173; 4,169,066; 4,207,893; 4,211,681; 4,271,143; 4,277,366; 4,327,725; 4,449,983; and, 4,800,056; and in *Handbook of Common Polymers*, by Scott and Roff, published by the Chemical Rubber Company, Cleveland, Ohio. The amount of hydrophilic polymer 23 present in second composition comprises 20 wt % to 85 wt %.

Layer 16 optionally comprises an osmagent 24, also known as an osmotically effective solute or osmotically effective compound. The osmagent 24 can be blended homogeneously or heterogeneously with the swellable polymer 23, to form a push member. The osmotically effective solutes are soluble in fluid imbibed into the swellable polymer, and exhibit an osmotic pressure gradient across the semipermeable wall against an exterior fluid. Osmotically effective osmagents useful for the present purpose include solid compounds selected from the group consisting of magnesium sulfate, magnesium chloride, sodium chloride, lithium chloride, potassium sulfate, sodium sulfate, mannitol, urea, sorbitol, inositol, sucrose, glucose and the like. The osmotic pressure in atmospheres, ATM, of the osmagents suitable for the invention with be greater than zero ATM, generally from zero ATM up to 500 ATM, or higher. The amount of osmagent blended with hydrophilic polymer 23 is 0 wt % to 65 wt %, and in one manufacture 7.5 wt % to 35 wt %.

Layer 16 preferably comprises 0 to 4.5 wt %, preferably 0.01 wt % to 4.5 wt % of a lubricant 25 such as stearic acid and the like; 0 wt % to 1 wt % of a dye 26 such as D&C yellow No. 10, and/or 0 wt % to 1 wt % of a second dye such as FD&C Blue No. 1; and 2.5 wt % to 30 wt % of a binder 27 such as polyvinyl-pyrrolidone, starch, gelatin, dextrose, lactose, molasses, mucilage, waxes and polyethylene glycol.

A port (or exit means) 13 is provided through wall 12 adjacent to the beneficial agent containing layer 15 for delivering the drug in the dosage form 10 into the mouth. The expression, "exit means," as used herein, comprises means and methods suitable for the controlled metered release of beneficial agent 17 from compartment 14 of dosage form 10. The exit means comprises at least one passageway, or the like, through wall 12 for communicating with compartment 14. The expressions, "at least one passageway," comprises aperture, orifice, bore, pore, porous element, hollow fiber, capillary tube, porous overlay, porous insert, and the like. The expression also comprises a material that erodes or is leached from the wall in a fluid environment of use to produce at least one passageway in the wall. Representative materials suitable for forming at least one passageway, or a multiplicity of passageways, comprise erodible polymers such as polyglycolic acid or a polylactic acid member in the wall, a gelatinous filament, polyvinyl alcohol, leachable materials, such as fluid removable pore-forming polysaccharides, salts, oxides or the like. A plurality of passageways can be formed by leaching a material such as sorbitol, lactose, or the like from the wall. The passageway can have any shape, such as round, triangular, square, elliptical, slit, and the like. Dosage form 10 can be constructed with one or more passageways in spaced apart relations, or more than one passageway in spaced apart relations, or more than one passageway on a single surface of dosage form 10. Passageways and equipment for forming passageways are disclosed in Theeuwes et al, U.S. Pat. No. 3,845,770, issued November, 1974; Theeuwes et al, U.S. Pat. No. 3,916,899, issued November, 1975; Saunders et al, U.S. Pat. No. 4,063,064, issued December, 1977; and Theeuwes et al, U.S. Pat. No. 4,088,864, issued May, 1978. Passageways in osmotic systems formed by leaching, to provide controlled-release bores, are disclosed in Ayer et al, U.S. Pat. No. 4,200,098, issued April 1980; Ayer et al, U.S. Pat. No. 4,285,987, issued August, 1981; Theeuwes, U.S. Pat. No. 4,309,996, issued January, 1982; and Theeuwes, U.S. Pat. No. 4,320,759, issued March, 1982.

The bilayer tablet 15/16 of dosage form 10 is manufactured by standard manufacturing techniques. For example, in one manufacture, beneficial agent and other ingredients comprising the first layer 15 facing the exit means are blended and pressed into a solid layer. The beneficial agent and other ingredients can be blended also with a solvent and mixed into a solid or semisolid form by conventional methods, such as ball-milling, calendering, stirring or rollmilling, and then pressed into a preselected shape. The first layer possesses dimensions that correspond to the internal dimensions of the area the layer is to occupy in the dosage form and it also possesses dimensions corresponding to the second layer for forming a contacting arrangement therewith. Next, the osmopolymer or hydrogel second layer is placed in contact with the beneficial agent's first layer. The layering of the beneficial agent layer and the osmopolymer layer can be fabricated by conventional press-layering techniques. Finally, the two layered compartment forming members that represent the first and second compositions are surrounded and coated with an outer wall. A passageway is laser drilled through the wall to contact the beneficial agent layer, with the dosage form optically oriented automatically by the laser equipment for forming the passageway on the preselected surface.

In another manufacture, the dosage form is manufactured by the wet granulation technique. In the wet granulation technique, the beneficial agent and the ingredients comprising the first layer are blended, using an organic or inorganic solvent, such as isopropyl alcohol-methylene dichloride 80/20 v/v as the granulation fluid. Other granulation fluids, such as water or denatured alcohol 100%, can be used for this purpose. The ingredients forming the first layer are individually passed through a 40 mesh screen and then thoroughly blended in a mixer. Next, other ingredients comprising the first layer are dissolved in a portion of the granulation fluid, such as the cosolvent described above. Then, the latter prepared wet blend is slowly added to the beneficial agent blend with continual mixing in the blender. The granulating fluid is added until a wet blend is produced, which wet mass then is forced through a 20 mesh screen onto oven trays. The blend is dried for 12 to 24 hours at 30° C. to 50° C. The dry granules are sized then with a 20 mesh screen. Next, a lubricant is passed through an 80 mesh screen and added to the dry screened granule blend. The granulation is put into milling jars and mixed on a jar mill for 10 to 15 minutes. The composition is pressed into layers, for example, in a Manesty® press layer press. The second layer is pressed in a similar manner.

Another manufacturing process that can be used for providing the compartment-forming composition comprises blending the powdered ingredients in a fluid bed granulator. After the powdered ingredients are dry blended in the granulator, a granulating fluid, for example poly (vinylpyrrolidone) in water, is sprayed onto the powders. The coated powders are then dried in a granulator. This process granulates all the ingredients present therein while adding the granulating fluid. After the granules are dried, a lubricant, such as stearic acid or magnesium stearate is blended, as above, into the mixture. The granules are pressed then in the manner described above.

Wall 12 of osmotic dosage form 10 can be formed by spraying wall 12 forming composition onto the bilayer tablets (i.e., tablets comprised of layers 15 and 16) which are suspended by tumbling in a heat dryer until the wall 12 is formed. The spraying and suspension procedure is described in U.S. Pat. No. 2,799,241; *J. Pharm. Assoc.*, Vol. 48, pages 451 to 459, (1959); and ibid, Vol. 49, pages 82 to 84, (1960). Dosage form 10 can also be coated with a wall-forming composition in a Wurster® air suspension coater, using acetone-water cosolvent, 90:10, wt:wt, using 2.5 to 4 wt % solids. The Aeromatic® air suspension coater using a methylene dichloride methanol cosolvent, 87:13, v:v, also can be used for applying the wall. Other wall forming techniques such as pan coating can be used for providing dosage form 10. In the pan coating system, wall forming compositions am deposited by successive spraying of the composition on the bilayered tablet, accompanying by tumbling in a rotating pan. A pan coater is used to produce thicker walls. A larger volume of methanol can be used in a cosolvent to produce a thinner wall. Finally, the wall coated compartments are dried in a forced air oven at 30° C. to 50° C. for up to a week to free the dosage form of solvent. Generally, the walls formed by these techniques have a thickness of 2 to 20 mils with a presently preferred thickness of 4 to 10 mils.

Exemplary solvents suitable for manufacturing the wall, the laminates and laminae, include inert inorganic and organic solvents that do not adversely harm the materials and the final wall of the final laminated wall. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethylacetate, methylene dichloride, ethylene dichloride, propylene dichloride, carbon tetrachloride, chloroform, nitrethane, nitropropane, tetrachloroethane, ethyl ether, isopropyl ether, cyclohexane, cyclo-octane, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

In one embodiment for treating painful conditions in the oral cavity, beclomethasone dipropionate is the agent employed in oral dosage form 10. In this embodiment, the oral dosage form 10 may contain 200 µg to 250 µg beclomethasone dipropionate, 0.15 weight % of beneficial agent formulation. Preferably, when treating painful conditions in the oral cavity, the device releases beclomethasone at the rate of about 0.1 mg/hr to about 1 mg/hr over the extended delivery period. Most preferably the device releases beclomethasone at 50–100 µg/hour for 3 hours. A device containing belcomethasone dipropionate can be administered one to three times per day for approximately 7 to 14 days.

Most preferably, beneficial agent formulation layer and expandable driving member having a length along the major axis of between 1.27 cm and 1.30 cm and a length along the minor axis of between 0.70 cm and 0.73 cm. Larger sizes, e.g. 1.58 cm, tend to result in membrane walls, which have adequate fluxes, but without sufficient structural integrity resulting in fracturing. Small size (0.953 cm) tend to be swallowed. The wall can be applied by molding, spraying, dipping, or air suspending the pressed shapes into a wall forming material.

The expressions "extended period of time" and "extended delivery period" as used herein generally refer to periods greater than about 0.5 hours, preferably about 1–3 hours, most preferably about 3 hours.

The following examples are merely illustrative of the present invention and should not be considered as limiting the scope of the invention in any way.

EXAMPLE 1

An oral dosage form manufactured in the form of an oral delivery device for delivering beclomethasone dipropionate into the oral cavity for treating painful conditions of the oral cavity, e.g. canker sores, was manufactured as follows: first, a 150 mg composition comprising 0.15% beclomethasone dipropionate, 43.75% hydroxypropyl cellulose (Klucel EF), 40.69% mannitol, 5.00% polyvinyl pyrrolidone K29-32, 5.00% propylene glycol alginate (PGA) and 0.50% magnesium stearate was prepared by standard wet granulation by blending the ingredients into a homogenous blend, and then lightly pressing the blend into a solid mass in a commercially available Manesty® tableting machine.

Next, a 100 mg composition containing 55.0% kappa carrageenan, 15.0% polyvinyl pyrrolidone K29-32, 28.0% sorbitol, 0.3% FD&C Blue #1, 0.07% D&C Yellow #10 and 1.0% stearate acid was blended together and added to the tableting machine. The driving member and beclomethasone dipropionate formulation were layered, sized to fit within and then pressed together by a ½ inch oval punch with a pressure head of 2 tons to form the tablet.

Then, the two layered mass was spray-coated in a Freud Hi-coater pan-coater with a semipermeable polymeric membrane wall formed from a 4% solids solution consisting of 70 wt % cellulose acetate having an acetyl content of 39.8%, in a solvent consisting of 95% acetone and 5% water, and is 30 wt % polyethylene glycol having a molecular weight of 3,350. The resulting semipermeable wall had a thickness of 3 mils (0.076 mm). One osmotic passageway, having a diameter of 20 mils, was drilled through the wall facing the beclomethasone dipropionate-containing layer for delivering it from the device. The membrane weight per core is about 27 mg.

The device was overcoated with a composition comprising in weight %, 40% benzocaine, 45% hydroxypropylmethylcellulose (HPMC 603) and 10% hydroxypropyl cellulose (Klucel EF), using ethanol/water (67/33%, wt/wt) as a mixed solvent. The overcoat weight per system was about 37.5 mg and was generally about 3 mils thick.

Figure 4:
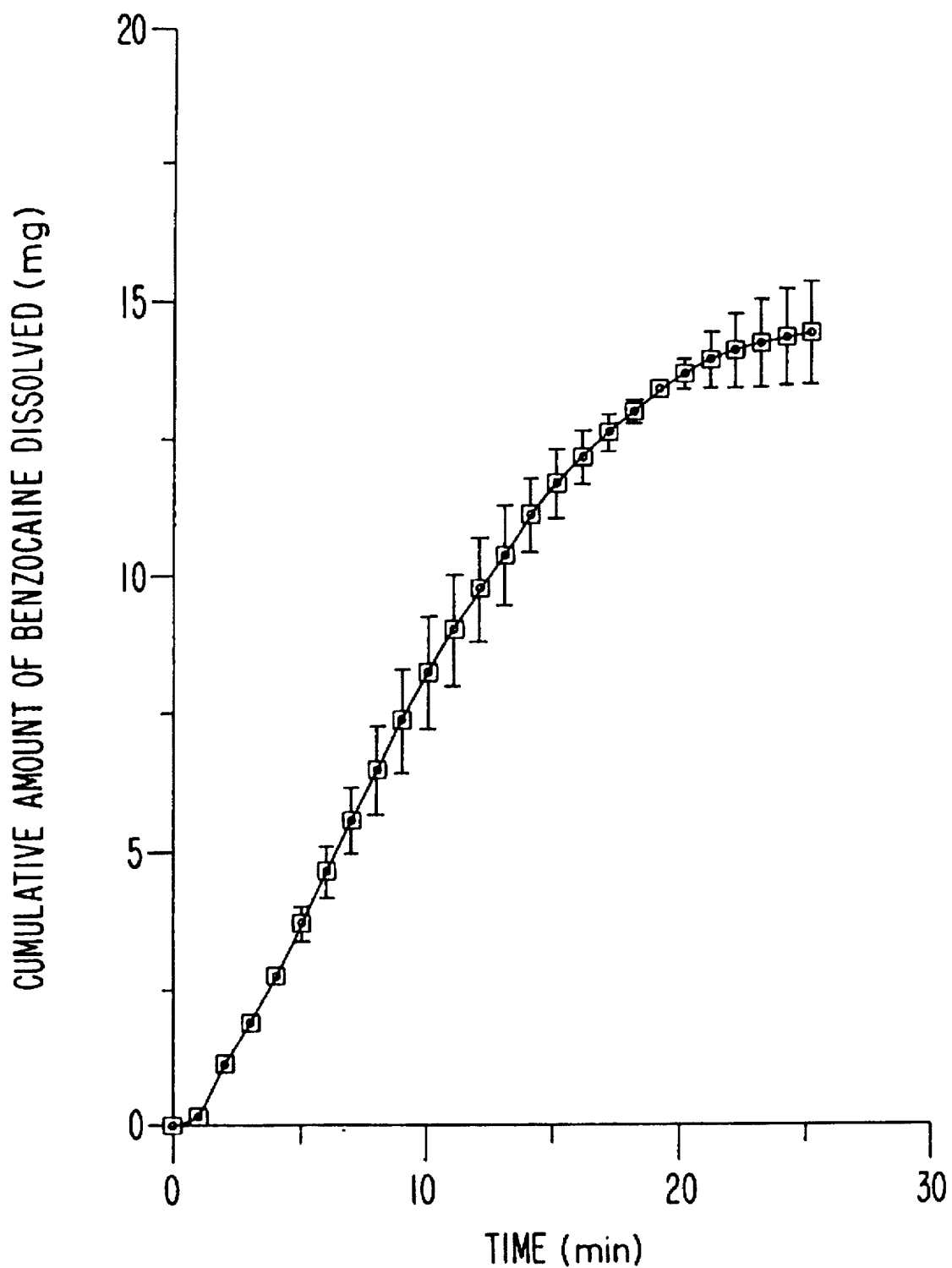
FIG. 4 is a graph illustrating the cumulative amount of benzocaine released from the overcoat layer of a device according to the present invention.
Figure 5:
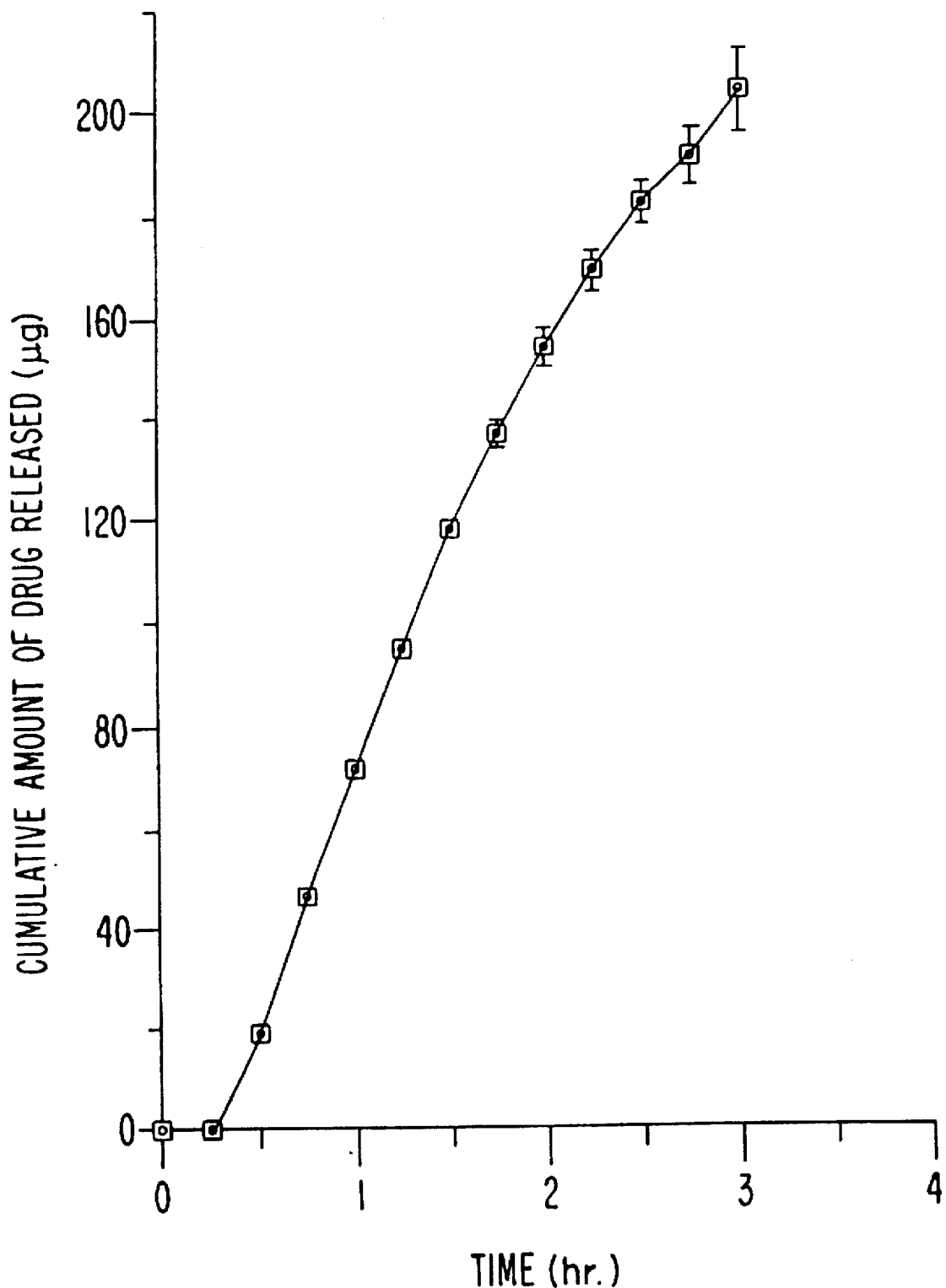
FIG. 5 is a graph illustrating the cumulative amount of beneficial agent released from a device according to the present invention.

The system delivers benzocaine rapidly in-vitro, with 15 mg of benzocaine released in about 15 minutes (FIG. 4). The release of beclomethasone over a four hour time period when placed in water at 37° C. is shown in FIG. 5, generally delivering 90% of the beneficial agent within 3 hours at an average rate of 66 µm/hr.

EXAMPLE 2

Figure 6:
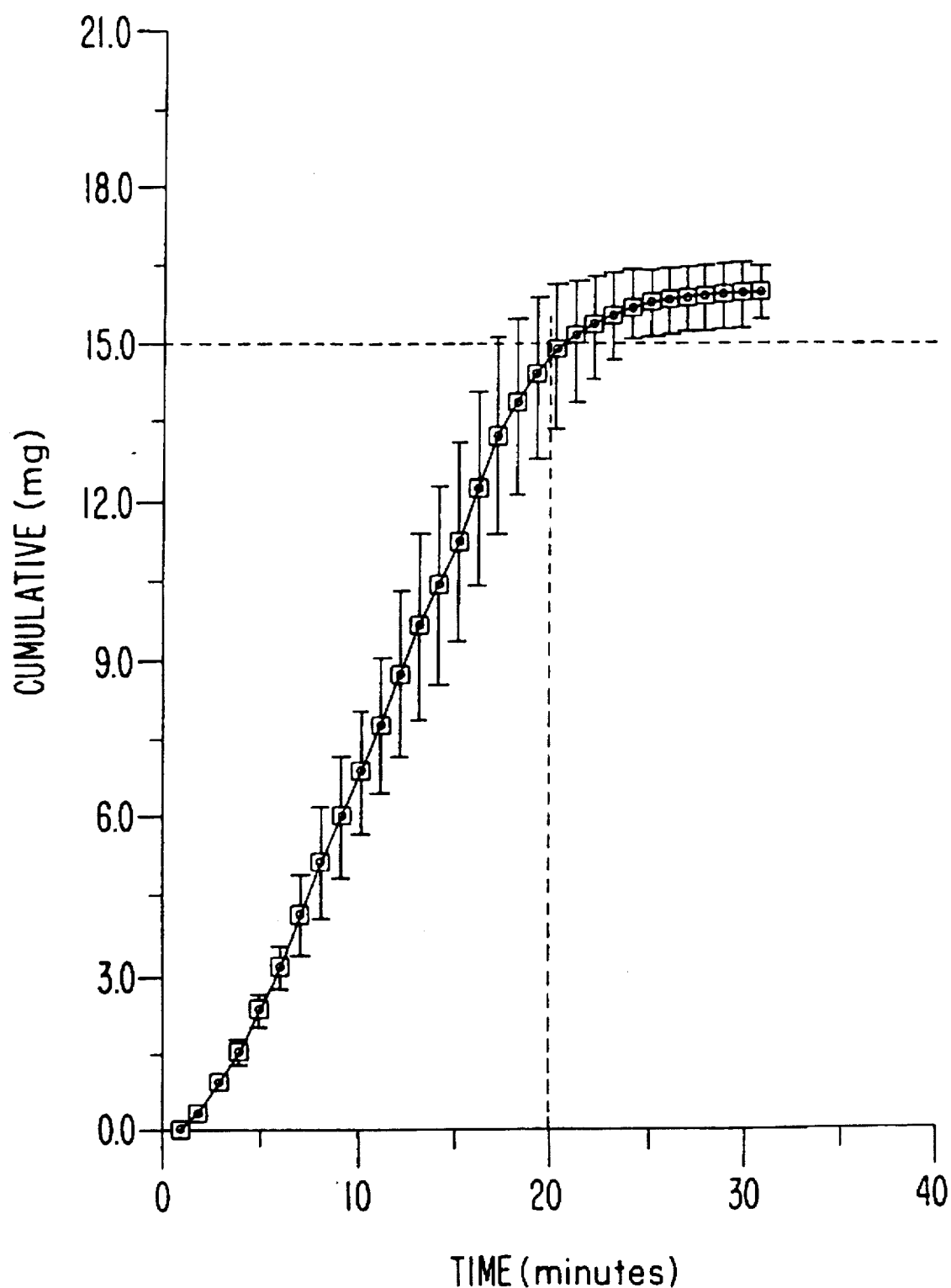
FIG. 6 is a graph illustrating the cumulative amount of benzocaine released from a device according to the present invention.

The procedure of Example 1 is repeated in this example for providing the following dispensing oral dosage form 10:

A delivery oral dosage form 10 is composed of the sustained release core 9 described with respect to Example 1. In addition, in this example, the overcoat 8 has a composition of 50% benzocaine, 37.5% HPMC 606 and 12.5% HPC (Klucel EF). The overcoat weighed 30 mg. The release profile of benzocaine from the overcoat is shown in FIG. 6.

What is claimed is:

1. A method for treating a site of a painful condition in the oral cavity which comprises:

applying an oral dosage form to the site of the painful condition, the oral dosage form including a topical anesthetic and a non-anesthetic beneficial agent; anesthetizing the site of the condition by immediately releasing the topical anesthetic from the dosage form; and continuously applying the non-anesthetic beneficial agent from the dosage form to the anesthetized site, wherein the release of the anesthetic is substantially independent of the release of the beneficial agent.

2. The method of claim 1, wherein about 90% of the non-anesthetic beneficial agent is delivered to the anesthetized site within a time period of about 1.0 to 3 hours.

3. The method of claim 1, wherein release of the anesthetic at the site of the condition provides pain relief from about 0.1 to 10 minutes.

4. The method of claim 1, wherein the topical anesthetic is substantially completely released within 15 to 30 minutes.

5. The method of claim 1, wherein the non-anesthetic beneficial agent is continuously applied by a core of a beneficial agent adapted to deliver the beneficial agent over the extended delivery period.

6. The method of claim 5, wherein said core further comprises an osmotic delivery device comprising a semipermeable wall enclosing a beneficial agent and an expandable driving member.

7. A method according to claim 5, wherein the beneficial agent is continuously applied at a rate of between 50 to 100 µg/hour over the delivery period.

8. A method according to claim 1, wherein the beneficial agent is an anti-inflammatory agent.

* * * * *